United States Patent
Lin et al.

(10) Patent No.: US 9,696,295 B2
(45) Date of Patent: Jul. 4, 2017

(54) METHOD FOR RAPIDLY DESIGNING PHARMACEUTICAL PREPARATIONS FOR PREVENTING VIRAL INFECTION

(71) Applicant: The Johns Hopkins University, Baltimore, MD (US)

(72) Inventors: Jeffrey S. Lin, Silver Spring, MD (US); Andrew S. Pekosz, Towson, MD (US); Andrew B. Feldman, Columbia, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 15/408,842

(22) Filed: Jan. 18, 2017

(65) Prior Publication Data
US 2017/0122933 A1 May 4, 2017

Related U.S. Application Data (62) Division of application No. 14/558,751, filed on Dec. 3, 2014, now Pat. No. 9,579,374.

(60) Provisional application No. 61/911,538, filed on Dec. 4, 2013.

(51) Int. Cl.
| | |
|---|---|
| *A61K 39/145* | (2006.01) |
| *G01N 33/50* | (2006.01) |
| *C07K 16/10* | (2006.01) |
| *C12N 7/00* | (2006.01) |

(52) U.S. Cl.
CPC ....... *G01N 33/5008* (2013.01); *A61K 39/145* (2013.01); *C07K 16/1018* (2013.01); *C12N 7/00* (2013.01); *C07K 2317/76* (2013.01); *C12N 2760/16021* (2013.01); *C12N 2760/16034* (2013.01)

(58) Field of Classification Search
None
See application file for complete search history.

(56) References Cited

U.S. PATENT DOCUMENTS

| | | |
|---|---|---|
| 5,162,112 A | 11/1992 | Oxford et al. |
| 8,389,297 B2 | 3/2013 | Pamula et al. |
| 2004/0265987 A1 | 12/2004 | Trager et al. |
| 2008/0014217 A1 | 1/2008 | Hanon et al. |
| 2009/0068637 A1 | 3/2009 | Xia et al. |
| 2009/0324645 A1 | 12/2009 | Pau et al. |
| 2010/0010199 A1 | 1/2010 | Tsai et al. |
| 2012/0164657 A1 | 6/2012 | Johnson et al. |
| 2012/0171120 A1 | 7/2012 | Dennis et al. |
| 2012/0207785 A1 | 8/2012 | Fabry et al. |

OTHER PUBLICATIONS

Cortez et al. PLoS Pathog 11(7): e1004973, pub 2015.*
Qiu et al. Clinical Immunology, vol. 141, Issue 2, Nov. 2011, pp. 218-227.*
Cortez, Valerie et al., "The Broad Neutralizing Antibody Responses after HIV-1 Superinfection Are Not Dominated by Antibodies Directed to Epitopes Common in Single Infection," PLOS Pathogens 11 (7): e1004973, pub 2015.
Qiu, Xiangguo et al., "Characterization of Zaire ebolavirus glycoprotein-specific monoclonal antibodies," Clinical Immunology, vol. 141, Issue 2, Nov. 2011, pp. 218-227.

* cited by examiner

*Primary Examiner* — Shanon A Foley
*Assistant Examiner* — Myron Hill
(74) *Attorney, Agent, or Firm* — Noah J. Hayward (57) ABSTRACT

Certain embodiments of the present invention include a method for rapidly designing pharmaceutical preparations for preventing viral infection that have adapted to growth in various culturing systems but maintain antigenic similarity to the original virus. The method may include serial passaging a plurality of instances of a targeted virus strain from an infected first animal in respective droplets in second animal cells, in parallel synthesizing antibodies that neutralize the targeted virus strain in a third animal, and selecting the second animal cell-adapted viral lineages that are neutralized by the antibodies to identify second animal cell-adapted viral lineages having antigenic similarity to the targeted virus strain.

10 Claims, 5 Drawing Sheets

FIGURE 1

201
Isolating Targeted Virus Strain From Infected First Animal

202
Serial Passaging Targeted Virus Strain From Step 201 in Droplets in Second Animal Cells To Form Second Animal Cell-Adapted Viral Lineages

203
Synthesizing Antibodies In Third Animal That Neutralize Targeted Virus Strain from Step 201

204
Selecting Second Animal Cell-Adapted Viral Lineages From Step 202 That Are Neutralized By Antibodies From Step 203 To Identify Second Animal Cell-Adapted Viral Lineages From Step 202 Having Antigenic Similarity To Targeted Virus Strain From Step 201

205
Replicating Second Animal Cell-Adapted Viral Lineages Having Antigenic Similarity To Targeted Virus Strain From Step 204 In Culturing System

FIGURE 2

```
┌─────────────────────┐
│         301         │
│  Inoculating Third  │
│ Animal With Targeted│
│    Virus Strain     │
└──────────┬──────────┘
           ▼
┌─────────────────────┐
│         302         │
│ Screening Third Animal│
│   PBMC For Antibodies│
│ That Neutralize Targeted│
│ Virus Strain From Step│
│         301         │
└──────────┬──────────┘
           ▼
┌─────────────────────┐
│         303         │
│ Sequencing Antibodies│
│    From Step 302    │
└──────────┬──────────┘
           ▼
┌─────────────────────┐
│         304         │
│Synthesizing Antibodies│
│ Sequenced In Step 303│
└─────────────────────┘
```

FIGURE 3

401
Running Drop-Based Neutralization or Affinity Assay on Second Animal Cell-Adapted Viral Lineages To Identify Second Animal Cell-Adapted Viral Lineages Neutralized By Antibodies

402
Inoculating Fourth Animal With Second Animal Cell-Adapted Viral Lineages Neutralized By Antibodies From Step 401 To Generate Antisera

403
Running Hemagglutination Inhibition Assay To Validate Second Animal Cell-Adapted Viral Lineages For Generating Antisera From Step 402 That React Positively To Targeted Virus Strain

METHOD FOR RAPIDLY DESIGNING PHARMACEUTICAL PREPARATIONS FOR PREVENTING VIRAL INFECTION

CROSS-REFERENCE TO RELATED APPLICATIONS

This application is a divisional of co-pending U.S. Nonprovisional application Ser. No. 14/558,751 filed on Dec. 3, 2014, which claims priority to and the benefit of U.S. Provisional Application Ser. No. 61/911,538 filed on Dec. 4, 2013, now expired, the contents of both of which are hereby incorporated herein by reference in their entireties.

STATEMENT OF GOVERNMENTAL INTEREST

This invention was made with government support under contract number HR0011-11-C-0093 awarded by the Defense Advanced Research Projects Agency (DARPA). The government has certain rights in the invention.

TECHNICAL FIELD

Example embodiments of the presently disclosed invention relate generally to a method for rapidly designing viral vaccines.

BACKGROUND

Influenza viruses are three genera of genetically diverse single-stranded RNA, enveloped viruses in the Orthomyxoviridae family. Influenza spreads worldwide in seasonal epidemics, resulting in about three to five million cases of severe illness and 250,000 to 500,000 deaths annually. Influenza is known to be transmitted through the air by coughs and sneezes, through direct contact with bird droppings or nasal secretions, or through contact with contaminated surfaces. Influenza infection is characterized by fever, chills, cough, nasal congestion, runny nose, sneezing, body aches, fatigue, headache, watering eyes, reddened skin, and petechiae.

Other exemplary viruses include norovirus, dengue, and Ebola. Norovirus, for example, is a genus of genetically diverse single-stranded RNA, non-enveloped viruses in the Caliciviridae family. Norovirus is known to be transmitted by fecally-contaminated food or water, by person-to-person contact, and via aerosolization of the virus and subsequent contamination of surfaces. Noroviruses are the most common cause of viral gastroenteritis in humans and affect people of all ages. Norovirus infection is characterized by nausea, forceful vomiting, watery diarrhea, abdominal pain, and in some cases, loss of taste. General lethargy, weakness, muscle aches, headache, and low-grade fever may occur. The disease is usually self-limiting, and severe illness is rare. However, the virus affects around 267 million people and causes over 200,000 deaths each year.

Furthermore, the dengue virus, for example, is a mosquito-borne single positive-stranded RNA virus of the family Flaviviridae, genus *Flavivirus*. The dengue virus in one of five serotypes is the cause of dengue fever, but all serotypes can cause the full spectrum of disease, including dengue fever, dengue hemorrhagic fever, and dengue shock syndrome. The dengue virus is known to be transmitted by several species of mosquito within the genus *Aedesa*, primarily *A. aegypti*. Dengue fever is characterized by fever, headache, muscle and joint pains, and a characteristic skin rash. Dengue hemorrhagic fever is characterized by bleeding, low levels of blood platelets, and blood plasma leakage, while dengue shock syndrome is characterized by myocardial depression, circumoral cyanosis, petechiae, hematemesis, melena, epistaxis, and possible pneumonia and/or myocarditis. The dengue virus infects 50 to 528 million people worldwide annually, leading to half a million hospitalizations and approximately 25,000 deaths.

Additionally, Ebola virus, for example, is a genus of genetically diverse single-stranded RNA, enveloped viruses in the Filoviridae family. Ebola typically occurs in outbreaks with 1,716 cases in 24 outbreaks through 2013. However, as of November 2014, the 2014 outbreak alone has resulted in 14,413 reported cases and 5,504 deaths. Ebola is known to be transmitted through direct contact with blood or other bodily fluids of an infected human or other animal. Ebola infection is characterized by fever, sore throat, muscle pain, headaches, vomiting, diarrhea, rash, impaired liver and kidney function, and internal and external hemorrhaging.

Vaccines are not currently commercially available for norovirus, dengue, or Ebola but are desperately needed. Influenza vaccines, however, have been manufactured for over 70 years using a process that involves infecting embryonated chicken eggs with influenza virus. The process is difficult to automate, labor-intensive, costly and creates significant risk of contamination. Another significant drawback to current vaccine manufacturing is poor virus yield. Moreover, viruses can often evolve or mutate over time. In some cases the evolution of viruses can occur rather rapidly, which makes screening, identification, and distribution of neutralizing antibodies in a timely and cost-effective manner particularly difficult. Furthermore, the currently used technologies described above do not guarantee that the developed vaccine will be effective against the original human-circulating strain or any of its close relatives. The developed vaccines may not be effective because the evolutionary adaptation of the virus during propagation in eggs during vaccine production may potentially change the surface proteins of the viruses such that they induce the production of antibodies that, while able to effectively neutralize the egg-adapted virus, do not neutralize the original human strain.

Therefore there at least remains a need in the art for a method for rapidly designing pharmaceutical preparations for preventing viral infection that have adapted to growth in various culturing systems but maintain antigenic similarity to the original virus.

BRIEF SUMMARY

One or more embodiments of the invention may address one or more of the aforementioned problems. Certain embodiments according to the present invention provide a method for rapidly designing pharmaceutical preparations for preventing viral infection in an affordable and efficient manner. In one aspect, certain embodiments of the invention provide a method for rapidly designing pharmaceutical preparations for preventing viral infection. The method may comprise serial passaging a plurality of instances of a targeted virus strain from an infected first animal in respective droplets in second animal cells so that the targeted virus strain adapts to the second animal cells to form second animal cell-adapted viral lineages, in parallel synthesizing antibodies that neutralize the targeted virus strain in a third animal, and selecting the second animal cell-adapted viral lineages that are neutralized by the antibodies to identify second animal cell-adapted viral lineages having antigenic similarity to the targeted virus strain.

In another aspect, example embodiments of the present invention provide a method for preventing viral infection. The method may comprise forming a pharmaceutical preparation for preventing viral infection and administering the pharmaceutical preparation to a subject in need thereof. In such embodiments, forming the pharmaceutical preparation may comprise serial passaging a plurality of instances of a targeted virus strain from an infected first animal in respective droplets in second animal cells so that the targeted virus strain adapts to the second animal cells to form second animal cell-adapted viral lineages, in parallel synthesizing antibodies that neutralize the targeted virus strain in a third animal, and selecting the second animal cell-adapted viral lineages that are neutralized by the antibodies to identify second animal cell-adapted viral lineages having antigenic similarity to the targeted virus strain.

BRIEF DESCRIPTION OF THE DRAWING(S)

Example embodiments of the present invention will be described more fully hereinafter with reference to the accompanying drawings, in which some, but not all embodiments of the invention are shown. Indeed, this invention may be embodied in many different forms and should not be construed as limited to the embodiments set forth herein; rather, these embodiments are provided so that this disclosure will satisfy applicable legal requirements. Like numbers refer to like elements throughout.

DETAILED DESCRIPTION

Example embodiments of the present invention now will be described more fully hereinafter with reference to the accompanying drawings, in which some, but not all embodiments of the inventions are shown. Indeed, this invention may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural referents unless the context clearly dictates otherwise.

Example embodiments of the present invention include a method for rapidly designing pharmaceutical preparations for preventing viral infection. For instance, this method may provide, for example, an affordable and efficient manner for generating large numbers of candidate virus strains for vaccines that induce production of antibodies that neutralize the original animal (e.g., human) virus strains. As such, for example, this method may permit development of vaccines that have adapted to growth in various culturing systems but maintain antigenic similarity to the original animal (e.g., human) virus.

Although influenza, norovirus, dengue, and Ebola are frequently referenced throughout this disclosure, these viruses serve only as an exemplary application of the present invention, which could be applicable to a wide variety of viral infections. Moreover, although embryonated eggs, human cells, non-human primate cells, MPCK cells, CHO cells, and BHK-21 cells are frequently referenced throughout this disclosure, these culturing systems serve only as an exemplary application of the present invention, which could be applicable to a wide variety of culturing systems. Furthermore, although humans and livestock are frequently referenced to throughout this disclosure, humans and livestock serve only as exemplary applications of the present invention, which could be applicable to a wide variety of animals.

As used herein, the terms "antibody" and "antibodies" may comprise a glycoprotein substantially encoded by an immunoglobulin gene or immunoglobulin genes, or fragments thereof, which specifically recognize and bind foreign molecules called antigens. The recognized immunoglobulin genes include the kappa, lambda, alpha, gamma, delta, epsilon, and mu constant region genes, as well as the immunoglobulin variable region genes. Antibodies include fragments, such as Fab', F(ab)$_2$, Fabc, and Fv fragments. Fab fragments are the antigen-binding domains of an antibody molecule. Fab fragments can be prepared by papain digestions of whole antibodies. Fv fragments are the minimal fragment (~30 kDa) that still contains the whole antigen-binding site of a whole IgG antibody. Fv fragments are composed of both the variable heavy chain ($V_H$) and variable light chain ($V_L$) domains. This heterodimer, called Fv fragment (for fragment variable) is still capable of binding the antigen. The term "antibody," as used herein, also includes antibody fragments either produced by the modification of whole antibodies or those synthesized de novo using recombinant DNA methodologies, and further includes "humanized" antibodies made by now conventional techniques.

The terms "antiserum" and "antisera", as used herein, may comprise blood serum that contains antibodies, as antitoxins or agglutinins, obtained by inoculation of animals and used for injection into other animals to provide immunity to a specific viral infection. Specifically, inoculating one animal with the infections agent, or "antigen", induces B-lymphocytes to produce IgG immunoglobulins specific for the antigen. The antibodies in the antiserum bind the antigen in the host, and the host immune system then recognizes foreign agents bound to the antibodies and triggers a more robust immune response.

The term "antigenic similarity", as used herein, may generally refer to a quantitative measure of how readily one amino acid residue can substitute for another in a protein-protein interaction, such as, for example, an antibody-antigen interaction. Two residues are very antigenically similar if substituting one for the other in a particular epitope has a small effect on the antigenic behavior of that epitope. Conversely, if the substitution has a large effect, then the two residues have a low antigenic similarity. In general, residues that have similar physical and chemical characteristics will have a high antigenic similarity.

The term "peripheral blood mononuclear cells (PBMC)", as used herein, may comprise any blood cell having a round nucleus. Such cells are known to play a role in the immune response. PBMC include for instance lymphocytes such as T cells, B lymphocytes and NK cells, monocytes, and macrophages. The PBMC may correspond to a B lymphocyte. The term "B lymphocyte" refers herein to B lymphocytes at any stage of differentiation, including naive B lymphocytes, mature B lymphocytes, memory B lymphocytes, B1 cells, B2 cells and plasma B lymphocytes. PBMC express markers at their cell surface, said markers differing from one PBMC population to another. For instance, B lymphocytes express CD19 at their cell surface, helper T cells express CD4 at their cell surface, cytotoxic T lymphocytes express CD8 at their cell surface, etc. As a consequence, a PBMC population may be detected through the use of an antibody specifically recognizing such a marker. A subpopulation of PBMC may express a given antibody specifically recognizing an antigen. As such, this subpopulation of PBMC is capable of specifically recognizing the antigen, in contrast to other PBMC that do not express the antibody.

The terms "serial passage" and "serial passaging", as used herein, may generally refer to the process of growing a virus in droplets in highly parallel iterations. The first passage is at a low multiplicity of infection. After several passages, the virus adapts to cell receptors. Physical separation of viruses in droplets during passaging allows genetic diversification without clonal sweep of dominant strains.

I. Method for Rapidly Designing Pharmaceutical Preparations

In one embodiment, the present invention provides a method for rapidly designing pharmaceutical preparations for preventing viral infection. For instance, this method may provide, for example, development of vaccines that have adapted to growth in various culturing systems but maintain antigenic similarity to the original animal (e.g., human) virus in an affordable and efficient manner. In general, methods for rapidly designing pharmaceutical preparations for preventing viral infection according to certain embodiments of the present invention may include serial passaging a plurality of instances of a targeted virus strain from an infected first animal in respective droplets in second animal cells so that the targeted virus strain adapts to the second animal cells to form second animal cell-adapted viral lineages, in parallel synthesizing antibodies that neutralize the targeted virus strain in a third animal, and selecting the second animal cell-adapted viral lineages that are neutralized by the antibodies to identify second animal cell-adapted viral lineages having antigenic similarity to the targeted virus strain.

In accordance with certain embodiments of the present invention, the second animal cells may comprise at least one of avian cells, human cells, non-human primate cells, or non-primate mammalian cells. In certain embodiments, for example, the second animal cells may comprise avian cells. According to certain embodiments of the present invention, the targeted virus strain may comprise a live virus, a dead virus, or combinations thereof. In certain embodiments, the targeted virus strain may comprise at least one of an influenza strain, a norovirus strain, a dengue strain, or an Ebola strain. In further embodiments, for example, the targeted virus strain may comprise an influenza strain. In such embodiments, for instance, the second animal cells may comprise avian cells.

In accordance with certain embodiments of the present invention, the method may comprise an initial operation of isolating the targeted virus strain from the infected first animal. In such embodiments, the infected first animal may comprise at least one of a human, a dog, a horse, a chicken, a cow, a pig, or another livestock animal. In certain embodiments, for example, the infected first animal may comprise a human. According to certain embodiments, for instance, livestock may comprise any farm animals except poultry including, but not limited to, cattle, sheep, pigs, goats, horses, donkeys, mules, buffalo, oxen, and camels.

In accordance with certain embodiments of the present invention, synthesizing antibodies that neutralize the targeted virus strain in the third animal may comprise inoculating a the third animal with the targeted virus strain, screening third animal peripheral blood mononuclear cells for antibodies that neutralize the targeted virus strain, sequencing the antibodies that neutralize the targeted virus strain, and synthesizing the antibodies that neutralize the targeted virus strain. In such embodiments, the third animal may comprise a mouse. According to certain embodiments, synthesizing antibodies may comprise rapid screening for therapeutic antibodies against, for example, human influenza strains in mice. After determining which antibodies bind to human influenza strains, the human influenza neutralizing antibody genes can be sequenced. Non-limiting examples of nucleic acid sequencing techniques include, but are not limited to, chain terminator (Sanger) sequencing and dye terminator sequencing, as well as "second generation" sequencing techniques.

The so-called "second-generation sequencing" or "next-generation sequencing" (NGS) techniques have emerged as alternatives to Sanger and dye-terminator sequencing methods and can be beneficially utilized in certain embodiments according to the present invention. NGS methods share the common feature of massively parallel, high-throughput strategies, with the goal of lower costs in comparison to older sequencing methods. NGS methods can be broadly divided into those that require template amplification and those that do not. Amplification-requiring methods include pyrosequencing commercialized by Roche as the 454 technology platforms (e.g., GS 20 and GS FLX), the Solexa platform commercialized by Illumina, and the Supported Oligonucleotide Ligation and Detection (SOLiD) platform commercialized by Applied Biosystems. Non-amplification approaches, also known as single-molecule sequencing, are exemplified by the HeliScope platform commercialized by Helicos BioSciences, and emerging platforms commercialized by VisiGen, Oxford Nanopore Technologies Ltd., and Pacific Biosciences, respectively.

In pyrosequencing, template DNA is fragmented, end-repaired, ligated to adaptors, and clonally amplified in-situ by capturing single template molecules with beads bearing oligonucleotides complementary to the adaptors. Each bead bearing a single template type is compartmentalized into a water-in-oil microvesicle, and the template is clonally amplified using a technique referred to as emulsion PCR. The emulsion is disrupted after amplification and beads are deposited into individual wells of a picotitre plate functioning as a flow cell during the sequencing reactions. Ordered, iterative introduction of each of the four dNTP reagents occurs in the flow cell in the presence of sequencing enzymes and luminescent reporter such as luciferase. In the event that an appropriate dNTP is added to the 3' end of the sequencing primer, the resulting production of ATP causes a burst of luminescence within the well, which is recorded using a CCD camera. It is possible to achieve read lengths greater than or equal to 400 bases, and $1 \times 10^6$ sequence reads can be achieved, resulting in up to 500 million base pairs (Mb) of sequence. In accordance with certain embodiments of the present invention, the methods of the present invention utilize pyrosequencing.

In the Solexa-Illumina platform (e.g., MiSeq sequencing platform), sequencing data are produced in the form of shorter-length reads. In this method, single-stranded fragmented DNA is end-repaired to generate 5'-phosphorylated blunt ends, followed by Klenow-mediated addition of a single A base to the 3' end of the fragments. A-addition facilitates addition of T-overhang adaptor oligonucleotides, which are subsequently used to capture the template-adaptor molecules on the surface of a flow cell that is studded with oligonucleotide anchors. The anchor is used as a PCR primer, but because of the length of the template and its proximity to other nearby anchor oligonucleotides, extension by PCR results in the "arching over" of the molecule to hybridize with an adjacent anchor oligonucleotide to form a bridge structure on the surface of the flow cell. These loops of DNA are denatured and cleaved. Forward strands are then sequenced with reversible dye terminators. The sequence of incorporated nucleotides is determined by detection of post-incorporation fluorescence, with each fluor and block removed prior to the next cycle of dNTP addition. Sequence read length ranges from 36 nucleotides to over 50 nucleotides, with overall output exceeding 1 billion nucleotide pairs per analytical run.

In accordance with certain embodiments of the present invention, selecting the second animal cell-adapted viral lineages that are neutralized by antibodies may comprise running at least one of a drop-based neutralization assay or drop-based affinity assay on the second animal cell-adapted viral lineages. Antibody secreting cells can then, for instance, be rapidly isolated using droplet microfluidic technology in order to obtain, for example, human influenza neutralizing antibody gene sequences. Functional assays in a droplet microfluidics format using a sorter chip can isolate single mononuclear cells in blood and bone marrow, for example, which secrete human influenza neutralizing antibodies. Compartmentalization of single cells in microfluidic droplets enables the analysis of proteins released from or secreted by cells. Secreted antibodies can be detected rapidly, for example, by co-compartmentalizing single mouse hybridoma cells, a fluorescent probe, and single beads coated with human influenza neutralizing antibodies in droplets. The beads capture the secreted antibodies, and when the captured antibodies bind to the probe, the fluorescence becomes localized on the beads, thereby generating a clearly distinguishable fluorescence signal that enables droplet sorting. The microfluidic system described can be easily adapted for screening other intracellular, cell-surface, or secreted proteins and for quantifying catalytic or regulatory activities.

In accordance with certain embodiments of the present invention, the method may further comprise inoculating a fourth animal with the second animal cell-adapted viral lineages to generate antisera in the fourth animal. In such embodiments, the fourth animal may comprise at least one of a ferret, a non-human primate, an infected human, a mouse, a rat, a rabbit, a chicken, a goat, a guinea pig, a hamster, a horse, or a sheep. In certain embodiments, for example, the fourth animal may comprise a ferret. In such embodiments, for instance, the targeted virus strain may be an influenza strain. In further embodiments, for example, the fourth animal may comprise a non-human primate. In such embodiments, for instance, the fourth animal may be a macaque. In such embodiments, for example, the targeted virus strain may be an Ebola strain.

In accordance with certain embodiments of the present invention, the method may further comprise running a hemagglutination inhibition (HAI) assay to validate each second animal cell-adapted viral lineage for generating antisera that react positively to the targeted virus strain. According to certain embodiments, for instance, the second animal cell-adapted viral lineages pre-incubated with antisera are mixed with a suspension of purified erythrocytes (e.g., human, avian, equine, murine erythrocytes, etc.) depending on the type of targeted virus strain. After incubation of the mixture in V- or U-bottomed microwells, the visual effect can be two-fold: if the antisera are absent or unable to effectively block the virus, the latter links the erythrocytes into a dispersed, three-dimensional agglutinant, but if the antigen is effectively blocked or absent, then the erythrocytes (ERCs) sediment to the bottom of the vial, forming the characteristic bright pellet, or "button."

In accordance with certain embodiments of the present invention, the method may further comprise replicating the second animal cell-adapted viral lineages having antigenic similarity to the targeted virus strain in a culturing system. In such embodiments, the culturing system may comprise at least one of embryonated eggs, human cells, non-human primate cells, MPCK cells, CHO cells, BHK-21 cells, or combinations thereof. In certain embodiments, for instance, human cells may comprise at least one of HEK 239, PerC.6, A549, CAP, CAP-T, WI-38, or MRC-5 cells. According to some embodiments, for example, non-human primate cells may comprise Vero cells.

Figure 1:
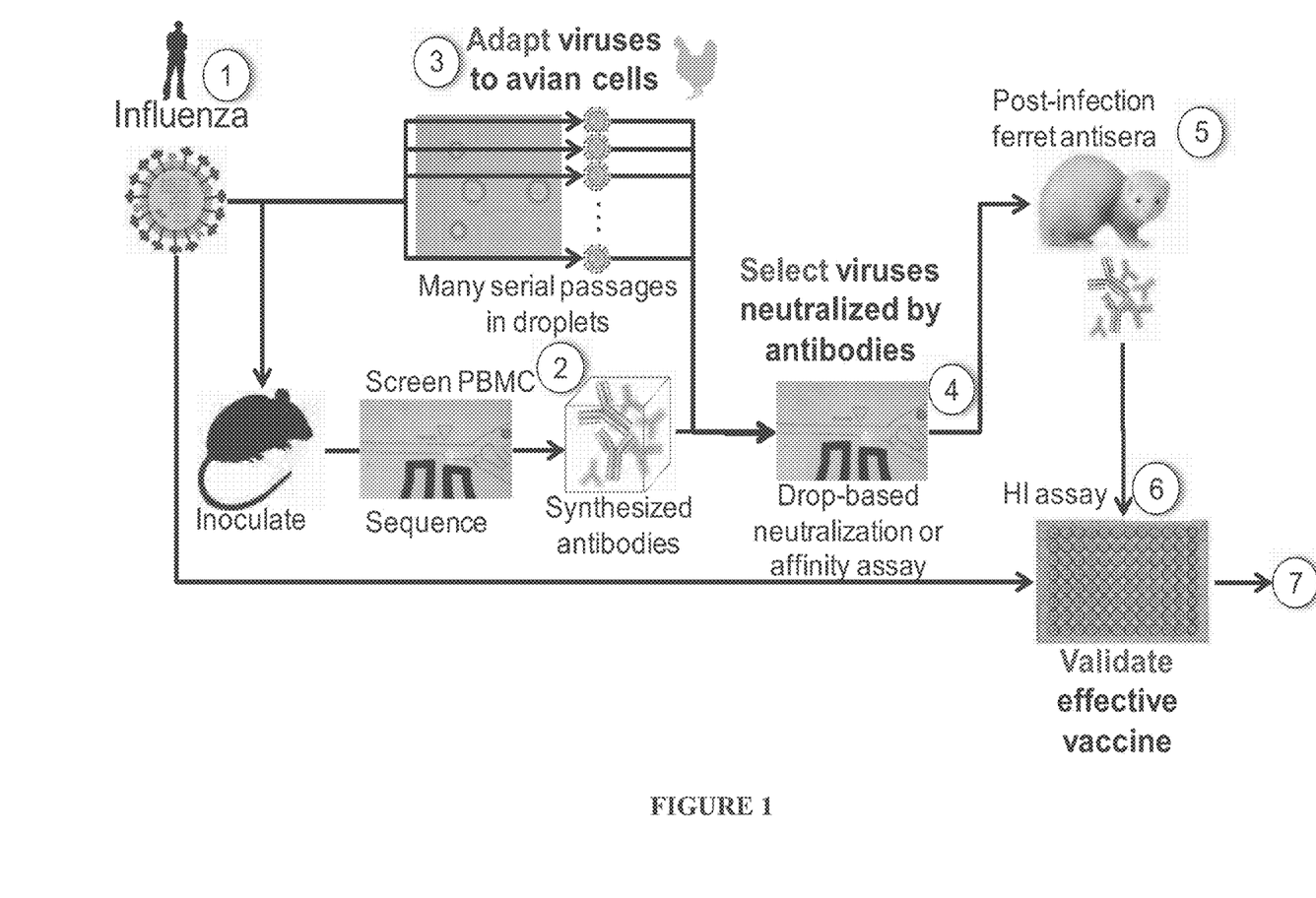
FIG. 1 illustrates an overview of a method for rapidly designing a pharmaceutical preparation for preventing viral infection according to certain embodiments of the present invention.

FIG. 1, for example, illustrates an overview of a method for rapidly designing a pharmaceutical preparation for preventing viral infection according to certain embodiments of the present invention. As shown in FIG. 1, the general method is highly parallel, with synthesizing antibodies occurring at substantially the same time as parallel serial passaging of viruses in droplets in avian cells in certain embodiments of the present invention.

Figure 2:
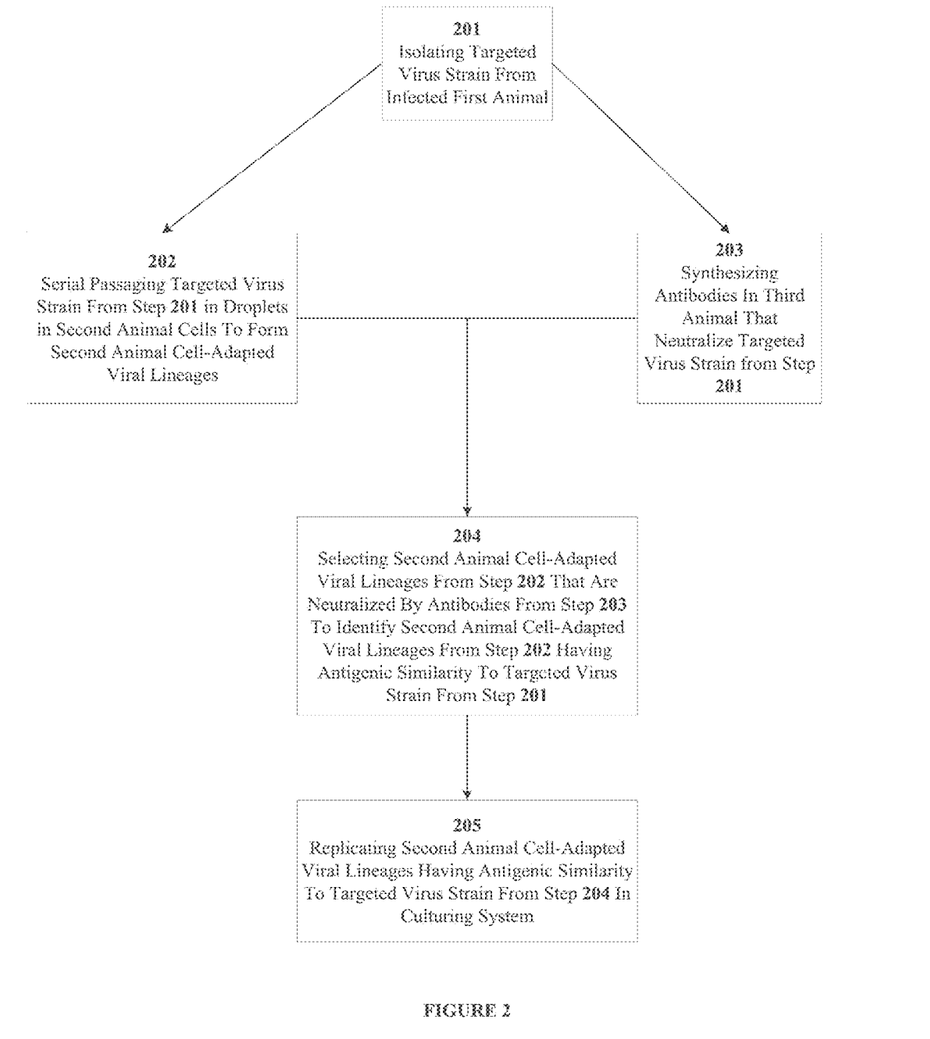
FIG. 2 illustrates a flow diagram for rapidly designing a pharmaceutical preparation for preventing viral infection according to certain embodiments of the present invention.

FIG. 2, for example, illustrates a flow diagram for rapidly designing a pharmaceutical preparation for preventing viral infection according to certain embodiments of the present invention. As shown in FIG. 2, the method comprises an initial isolating step 201, in which the targeted virus strain is isolated from an infected first animal. Next, a serial passaging step 202 and an antibody synthesis step 203 occur in parallel. In the serial passaging step 202, the targeted virus strain from step 201 is serial passaged in droplets in second animal cells to form second animal cell-adapted viral lineages. The antibody synthesis step 203 comprises synthesizing antibodies in a third animal so that the synthesized antibodies neutralize the targeted virus strain from step 201. The method further comprises step 204, which comprises selecting the second animal cell-adapted viral lineages from step 202 that are neutralized by the antibodies from step 203 in order to identify those second animal cell-adapted viral lineages from step 202 having antigenic similarity to the targeted virus strain isolated in step 201. The method further comprises step 205, which comprises replicating those second animal cell-adapted viral lineages having antigenic similarity to the targeted virus strain from step 204 in a culturing system.

Figure 3:
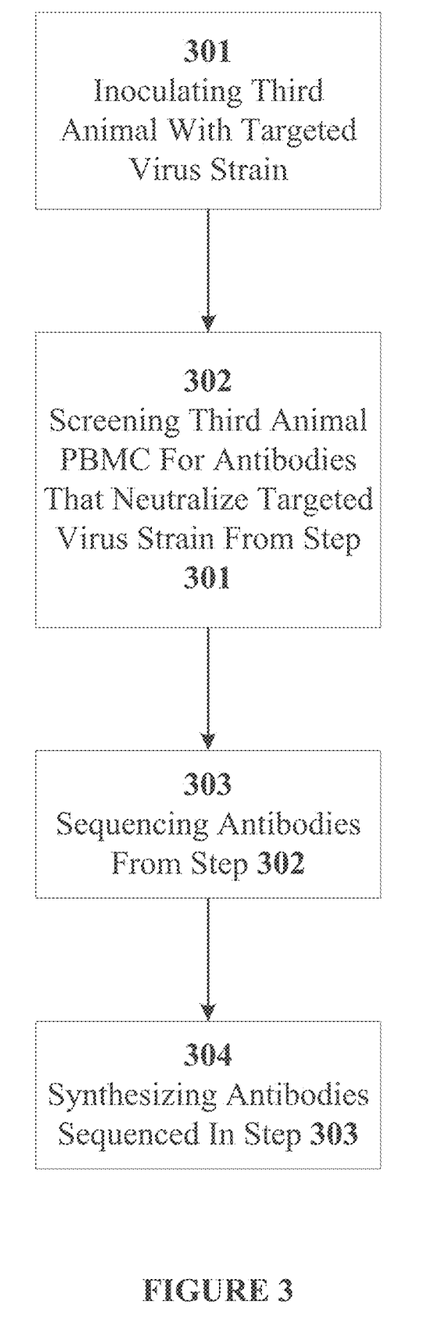
FIG. 3 illustrates a flow diagram for synthesizing antibodies according to certain embodiments of the present invention.

FIG. 3, for example, illustrates a flow diagram for synthesizing antibodies according to certain embodiments of the present invention. As shown in FIG. 3, synthesizing antibodies comprises an initial step 301 of inoculating a third animal with a targeted virus strain. The method further comprises step 302, which comprises screening the peripheral blood mononuclear cells of the third animal for antibodies that neutralize the targeted virus strain from step 301. Next, step 303 comprises sequencing the antibodies from step 302. The method further comprises step 304, which comprises synthesizing the antibodies sequenced in step 303.

Figure 4:
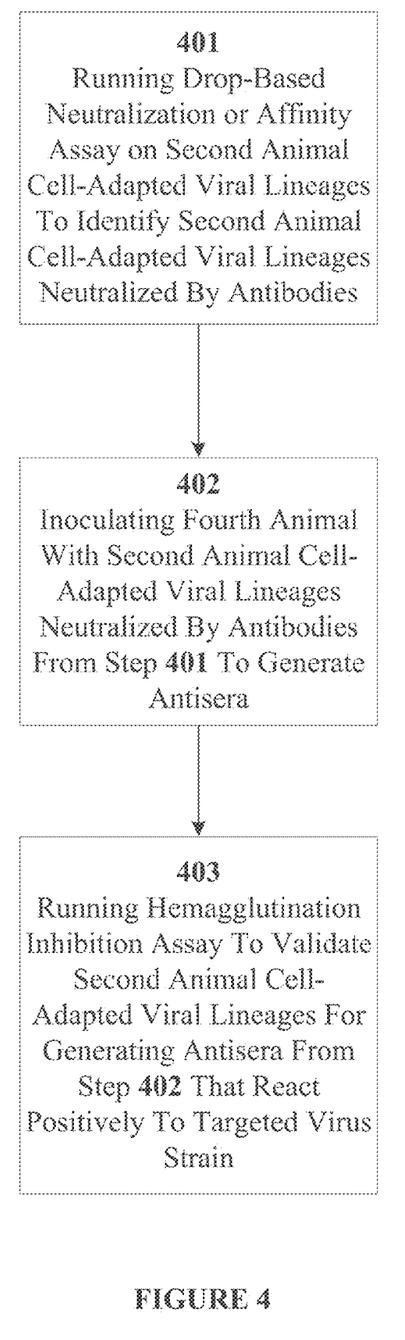
FIG. 4 illustrates a flow diagram for identifying second animal cell-adapted viral lineages having antigenic similarity to a targeted virus strain according to certain embodiments of the present invention.

FIG. 4, for example, illustrates a flow diagram for identifying second animal cell-adapted viral lineages having antigenic similarity to a targeted virus strain according to certain embodiments of the present invention. As shown in FIG. 4, identifying second animal cell-adapted viral lineages having antigenic similarity to a targeted virus strain comprises an initial step 401 of running drop-based neutralization assays or drop-based affinity assays on second animal cell-adapted viral lineages in order to identify those second animal cell-adapted viral lineages neutralized by antibodies. Next, the method comprises step 402, which comprises inoculating a fourth animal with those second animal cell-adapted viral lineages neutralized by antibodies from step 401 in order to generate antisera. The method further comprises step 403, which comprises running a hemagglutination inhibition assay in order to validate those second animal cell-adapted viral lineages for generating antisera from step 402 that react positively to the targeted virus strain.

II. Method for Preventing Viral Infection

In another embodiment, the present invention provides for methods for preventing viral infection. For instance, this method may provide, for example, for administration of vaccines that have adapted to growth in various culturing systems but maintain antigenic similarity to the original animal (e.g., human) virus in an affordable and efficient manner. In general, methods of preventing viral infection according to certain embodiments of the present invention may include forming a pharmaceutical preparation for preventing viral infection and administering the pharmaceutical preparation to a subject in need thereof. In certain embodiments, forming the pharmaceutical preparation for preventing viral infection may comprise serial passaging a plurality of instances of a targeted virus strain from an infected first animal in respective droplets in second animal cells so that the targeted virus strain adapts to the second animal cells to form second animal cell-adapted viral lineages, in parallel synthesizing antibodies that neutralize the targeted virus strain in a third animal, and selecting the second animal cell-adapted viral lineages that are neutralized by the antibodies to identify second animal cell-adapted viral lineages having antigenic similarity to the targeted virus strain. As such, the pharmaceutical preparation for preventing viral infection may be formed according to any of the embodiments disclosed in regard to the method for rapidly designing a pharmaceutical preparation for preventing viral infection.

In accordance with certain embodiments of the present invention, a wide variety of pharmaceutical preparations may be prepared. Pharmaceutical preparations may be in the form, for example, of tablets (e.g., enteric coated for time and/or pH release), syrups, elixirs, solutions (e.g., drinkable, inhalable, injectable, etc.), and capsules that can, for example, function as a vaccine. According to certain embodiments, for instance, the pharmaceutical preparation may be administered prophylactically.

Figure 5:
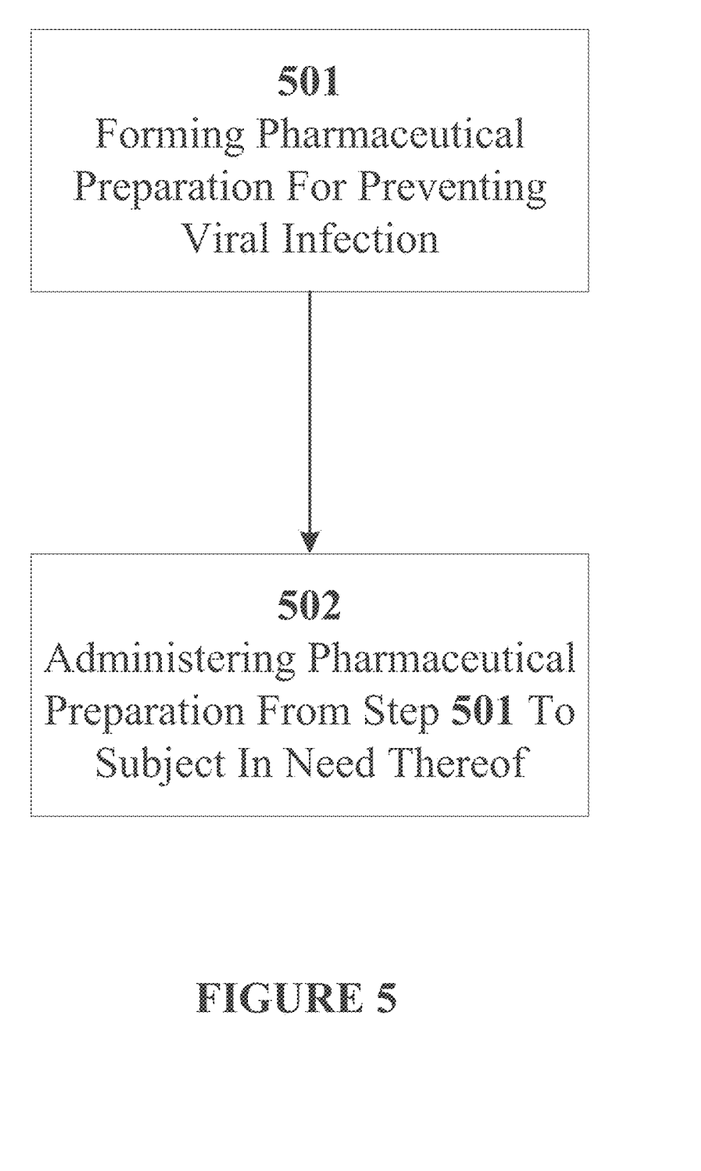
FIG. 5 illustrates a flow diagram for preventing viral infection according to certain embodiments of the present invention.

FIG. 5, for example, illustrates a flow diagram for preventing viral infection according to certain embodiments of the present invention. As shown in FIG. 5, preventing viral infection comprises an initial step 501 of forming a pharmaceutical preparation for preventing viral infection. The method for forming the pharmaceutical preparation according to certain embodiments of the present invention is illustrated in FIGS. 1-4. The method further comprises step 502, which comprises administering the pharmaceutical preparation from step 501 to a subject in need thereof.

Additional Exemplary Embodiments

Certain embodiments according to the present invention provide a method for rapidly designing pharmaceutical preparations for preventing viral infection. For instance, this method provides development of vaccines that have adapted to growth in various culturing systems but maintain antigenic similarity to the original animal (e.g., human) virus in an affordable and efficient manner. In one aspect, the method for rapidly designing pharmaceutical preparations for preventing viral infection according to certain embodiments of the present invention includes serial passaging a plurality of instances of a targeted virus strain from an infected first animal in respective droplets in second animal cells so that the targeted virus strain adapts to the second animal cells to form second animal cell-adapted viral lineages, in parallel synthesizing antibodies that neutralize the targeted virus strain in a third animal, and selecting the second animal cell-adapted viral lineages that are neutralized by the antibodies to identify second animal cell-adapted viral lineages having antigenic similarity to the targeted virus strain. In such embodiments, the second animal cells comprise at least one of avian cells, human cells, non-human primate cells, or non-primate mammalian cells.

In accordance with certain embodiments of the present invention, synthesizing antibodies that neutralize the targeted virus strain in the third animal comprises inoculating the third animal with the targeted virus strain, screening third animal peripheral blood mononuclear cells for antibodies that neutralize the targeted virus strain, sequencing the antibodies that neutralize the targeted virus strain, and synthesizing the antibodies that neutralize the targeted virus strain. According to certain embodiments, the third animal comprises a mouse.

In accordance with certain embodiments of the present invention, selecting second animal cell-adapted viral lineages that are neutralized by the antibodies comprises running at least one of a drop-based neutralization assay or drop-based affinity assay on the second animal cell-adapted viral lineages. In certain embodiments, selecting second animal cell-adapted viral lineages that are neutralized by the antibodies further comprises inoculating a fourth animal with the second animal cell-adapted viral lineages that are neutralized by the antibodies that neutralize the targeted virus strain to generate antisera in the fourth animal. In such embodiments, the fourth animal comprises at least one of a ferret, a non-human primate, an infected human, a mouse, a rat, a rabbit, a chicken, a goat, a guinea pig, a hamster, a horse, or a sheep. In some embodiments, selecting second animal cell-adapted viral lineages that are neutralized by the antibodies further comprises running a hemagglutination inhibition assay to validate each second animal cell-adapted viral lineage for generating antisera that react positively to the targeted virus strain.

In accordance with certain embodiments of the present invention, the method further comprises an initial operation of isolating the targeted virus strain from the infected first animal. In such embodiments, the infected first animal comprises at least one of a human, a dog, a horse, a chicken, a cow, a pig, or another livestock animal. In certain embodiments, the method further comprises replicating the second animal cell-adapted viral lineages having antigenic similarity to the targeted virus strain in a culturing system. In such embodiments, the culturing system comprises at least one of embryonated eggs, human cells, non-human primate cells, MPCK cells, CHO cells, BHK-21 cells, or combinations thereof.

In accordance with certain embodiments of the present invention, the targeted virus strain comprises a live virus, a dead virus, or combinations thereof. In certain embodiments, the targeted virus strain comprises at least one of an influenza strain, a norovirus strain, a dengue strain, or an Ebola strain.

In another aspect, certain embodiments according to the present invention provide a method for preventing viral infection. For instance, this method provides for administration of vaccines that have adapted to growth in various culturing systems but maintain antigenic similarity to the original animal (e.g., human) virus in an affordable and efficient manner. According to certain embodiments, the method includes forming a pharmaceutical preparation for preventing viral infection and administering the pharmaceutical preparation to a subject in need thereof. In certain embodiments, forming the pharmaceutical preparation for preventing viral infection comprises serial passaging a plurality of instances of a targeted virus strain from an infected first animal in respective droplets in second animal cells so that the targeted virus strain adapts to the second animal cells to form second animal cell-adapted viral lineages, in parallel synthesizing antibodies that neutralize the targeted virus strain in a third animal, and selecting the second animal cell-adapted viral lineages that are neutralized by the antibodies to identify second animal cell-adapted viral lineages having antigenic similarity to the targeted virus strain.

In accordance with certain embodiments of the present invention, synthesizing antibodies that neutralize the targeted virus strain in the third animal comprises inoculating the third animal with the targeted virus strain, screening third animal peripheral blood mononuclear cells for antibodies that neutralize the targeted virus strain, sequencing the antibodies that neutralize the targeted virus strain, and synthesizing the antibodies that neutralize the targeted virus strain.

In accordance with certain embodiments of the present invention, the targeted virus strain comprises at least one of a live virus, a dead virus, or combinations thereof. In certain embodiments, the targeted virus strain comprises at least one of an influenza strain, a norovirus strain, a dengue strain, or an Ebola strain.

In accordance with certain embodiments of the present invention, the infected first animal comprises at least one of a human, a dog, a horse, a chicken, a cow, a pig, or another livestock animal. In certain embodiments, the second animal cells comprise at least one of avian cells, human cells, non-human primate cells, or non-primate mammalian cells.

In accordance with certain embodiments of the present invention, forming pharmaceutical preparations further comprises an initial operation of isolating the targeted virus strain from the infected first animal. In certain embodiments, forming pharmaceutical preparations further comprises inoculating a fourth animal with the second animal cell-adapted viral lineages that are neutralized by the antibodies that neutralize the targeted virus strain to generate antisera in the fourth animal, running a hemagglutination inhibition assay to validate each second animal cell-adapted viral lineage for generating antisera that react positively to the targeted virus strain, and replicating the second animal cell-adapted viral lineages having antigenic similarity to the targeted virus strain in a culturing system. In such embodiments, the fourth animal comprises at least one of a ferret, a non-human primate, an infected human, a mouse, a rat, a rabbit, a chicken, a goat, a guinea pig, a hamster, a horse, or a sheep. In certain embodiments, the culturing system comprises at least one of embryonated eggs, human cells, non-human primate cells, MPCK cells, CHO cells, BHK-21 cells, or combinations thereof.

These and other modifications and variations to example embodiments of the present invention may be practiced by those of ordinary skill in the art without departing from the spirit and scope of the present invention, which is more particularly set forth in the appended claims. In addition, it should be understood that aspects of the various embodiments may be interchanged in whole or in part. Furthermore, those of ordinary skill in the art will appreciate that the foregoing description is by way of example only, and it is not intended to limit the invention as further described in such appended claims. Therefore, the spirit and scope of the appended claims should not be limited to the exemplary description of the versions contained herein.

What is claimed is:

1. A method for preventing influenza viral infection, the method comprising:
    (a) preparing a pharmaceutical preparation for preventing the influenza viral infection, wherein the preparing the pharmaceutical preparation comprises:
        (i) isolating an influenza targeted virus strain from a first animal;
        (ii) serial passaging a plurality of samples of the influenza targeted virus strain from the first animal in respective droplets in cells of a second animal, wherein the influenza targeted virus strain adapts to the cells of the second animal to form second animal cell-adapted viral lineages;
        (iii) in parallel to the serial passaging, synthesizing antibodies that neutralize the influenza targeted virus strain in a third animal, wherein the synthesizing comprises:
            (A) inoculating the third animal with the influenza targeted virus strain;
            (B) screening peripheral blood mononuclear cells of the third animal for antibodies that neutralize the influenza targeted virus strain;
            (C) sequencing the antibodies that neutralize the influenza targeted virus strain; and
            (D) synthesizing the antibodies sequenced in step (iii), and
        (iv) running at least one of a drop-based neutralization assay or drop-based affinity assay on the second animal cell-adapted viral lineages; and
        (v) selecting the second animal cell-adapted viral lineages that are neutralized by the antibodies to identify second animal cell-adapted viral lineages having antigenic similarity to the influenza targeted virus strain; and
    (b) administering the pharmaceutical preparation to a subject in need thereof.

2. The method according to claim 1, wherein the first animal comprises at least one of a human, a dog, a horse, a chicken, a cow, a pig, or another livestock animal.

3. The method according to claim 1, wherein the cells of the second animal comprise at least one of avian cells, human cells, non-human primate cells, or non-primate mammalian cells.

4. The method according to claim 1, wherein:
    a. the first animal comprises at least one of a human, a dog, a horse, a chicken, a cow, a pig, or another livestock animal; and b. the cells of the second animal comprise at least one of avian cells, human cells, non-human primate cells, or non-primate mammalian cells.

5. The method according to claim 1, wherein the preparing pharmaceutical preparations further comprises:
   a. inoculating a fourth animal with the second animal cell-adapted viral lineages that are neutralized by the antibodies that neutralize the influenza targeted virus strain to generate antisera in the fourth animal;
   b. running a hemagglutination inhibition assay to validate each second animal cell-adapted viral lineage for generating antisera that react positively to the influenza targeted virus strain; and
   c. replicating the second animal cell-adapted viral lineages having antigenic similarity to the influenza targeted virus strain in a culturing system.

6. The method according to claim 5, wherein the fourth animal comprises at least one of a ferret, a non-human primate, an infected human, a mouse, a rat, a rabbit, a chicken, a goat, a guinea pig, a hamster, a horse, or a sheep.

7. The method according to claim 5, wherein the culturing system comprises at least one of embryonated eggs, human cells, non-human primate cells, MPCK cells, CHO cells, BHK-21 cells, or combinations thereof.

8. The method according to claim 1, wherein the preparing the pharmaceutical preparation further comprises replicating the second animal cell-adapted viral lineages having antigenic similarity to the influenza targeted virus strain in a culturing system.

9. The method according to claim 8, wherein the culturing system comprises at least one of embryonated eggs, human cells, non-human primate cells, MPCK cells, CHO cells, BHK-21 cells, or combinations thereof.

10. The method according to claim 1, wherein the preparing the pharmaceutical preparation further comprises inoculating a fourth animal with the second animal cell-adapted viral lineages that are neutralized by the antibodies that neutralize the influenza targeted virus strain to generate antisera in the fourth animal.

* * * * *